(12) United States Patent
Umeda et al.

(10) Patent No.: US 8,613,735 B2
(45) Date of Patent: Dec. 24, 2013

(54) SUCTION DEVICE, SUCTION SYSTEM, AND SUCTION METHOD

(75) Inventors: Hiroo Umeda, Kyoto (JP); Shin-ichi Kanemaru, Kyoto (JP)

(73) Assignee: Kyoto University, Kyoto (JP)

( * ) Notice: Subject to any disclaimer, the term of this patent is extended or adjusted under 35 U.S.C. 154(b) by 695 days.

(21) Appl. No.: 12/670,427

(22) PCT Filed: Jul. 15, 2008

(86) PCT No.: PCT/JP2008/062733
§ 371 (c)(1),
(2), (4) Date: Mar. 31, 2010

(87) PCT Pub. No.: WO2009/014026
PCT Pub. Date: Jan. 29, 2009

(65) Prior Publication Data
US 2010/0198170 A1    Aug. 5, 2010

(30) Foreign Application Priority Data

Jul. 26, 2007  (JP) ................................. 2007-194634

(51) Int. Cl.
*A61M 1/00* (2006.01)
(52) U.S. Cl.
USPC ........... 604/319; 604/289; 604/290; 604/304; 604/305; 604/307; 604/308; 604/315; 604/316; 604/321; 604/322; 604/327; 604/540; 604/543
(58) Field of Classification Search
USPC ........................... 604/315, 316, 319, 321, 322
See application file for complete search history.

(56) References Cited

U.S. PATENT DOCUMENTS

| 3,771,527 A | 11/1973 | Ruisi |
| 4,935,006 A * | 6/1990 | Hasson .......................... 604/43 |
| 5,237,993 A | 8/1993 | Skrabal |
| 5,248,297 A | 9/1993 | Takase |
| 2004/0092956 A1 * | 5/2004 | Liddicoat et al. ............. 606/127 |

FOREIGN PATENT DOCUMENTS

| DE | 41 41 014 | 7/1993 |
| GB | 1 463 577 | 2/1977 |
| JP | 57-156208 | 9/1982 |
| JP | 61-98819 | 5/1986 |
| JP | 63-219510 | 9/1988 |
| JP | 5-220157 | 8/1993 |

(Continued)

OTHER PUBLICATIONS

Japan Office action, mail date is Mar. 12, 2013.

(Continued)

*Primary Examiner* — Tatyana Zalukaeva
*Assistant Examiner* — Ilya Treyger
(74) *Attorney, Agent, or Firm* — Greenblum & Bernstein P.L.C.

(57) ABSTRACT

A suction device according to the present invention has: an outer tube connected to a fluid supply unit on a base-end side thereof and including an opening edge section; and a suction tube provided in the outer tube and connected to a negative pressure generating unit on a base-end side thereof, the suction tube including an opening edge section, wherein an annular fluid supply passage is formed between an inner peripheral surface of the outer tube and an outer peripheral surface of the suction tube, and the opening edge section of the suction tube is placed inside the opening edge section of the outer tube toward the base-end side thereof.

9 Claims, 5 Drawing Sheets

(56) References Cited

FOREIGN PATENT DOCUMENTS

| | | |
|---|---|---|
| JP | 5-68545 | 9/1993 |
| JP | 6-105903 | 4/1994 |
| JP | 2742765 | 2/1998 |
| JP | 2001-98761 | 4/2001 |
| JP | 2001-321435 | 11/2001 |
| JP | 2005-137463 | 6/2005 |
| WO | 85/00016 | 1/1985 |

OTHER PUBLICATIONS

European Search Report, mail date is Jun. 21, 2013.

* cited by examiner

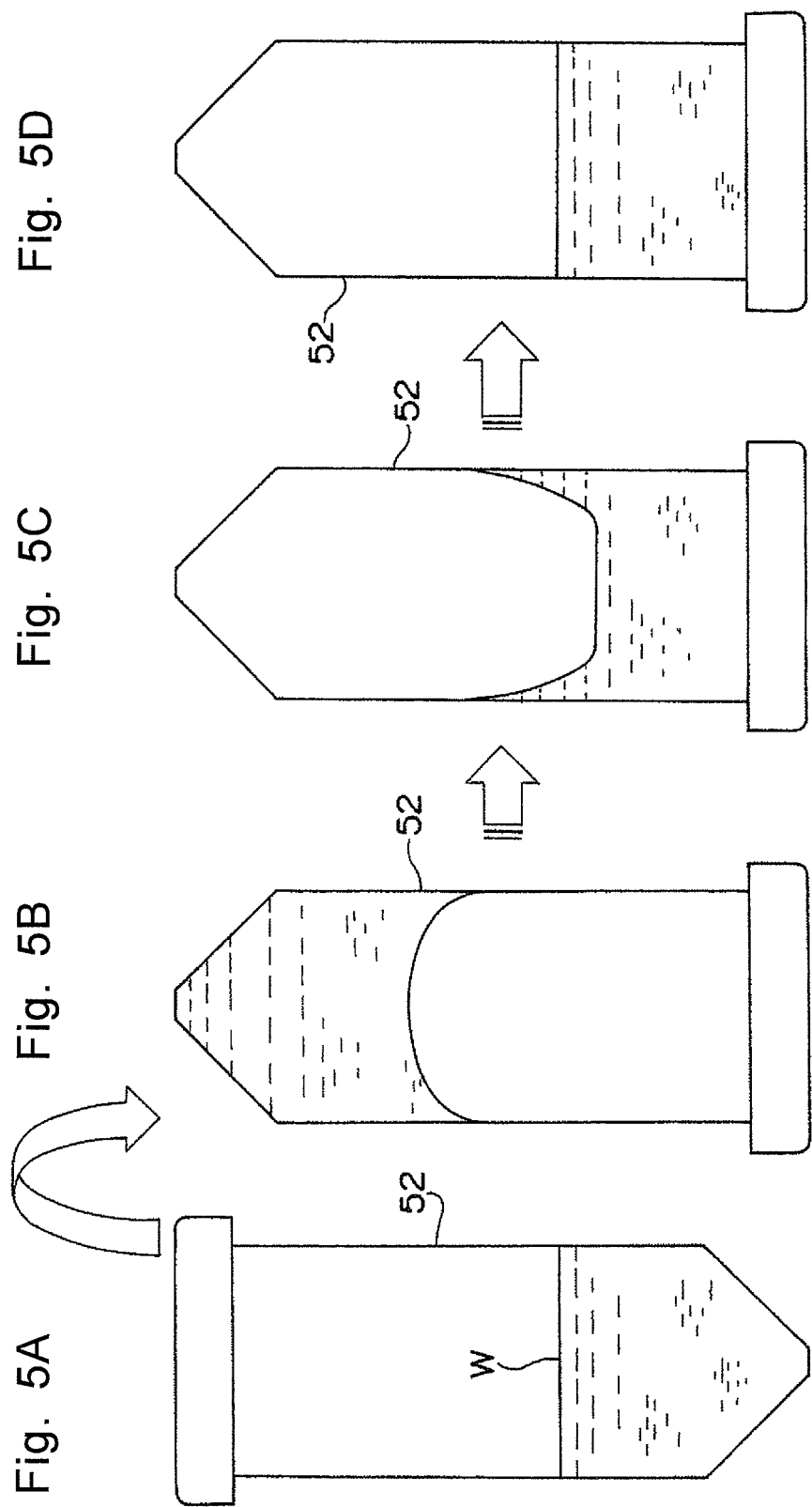

SUCTION DEVICE, SUCTION SYSTEM, AND SUCTION METHOD

BACKGROUND OF THE INVENTION

1. Technical Field

The present invention relates to a suction device, a suction system, and a suction method and, more particularly to a suction device, a suction system, and a suction method suitably used for sucking a viscous matter in clinical practice (for example, department of otorhinolaryngology).

2. Background Art

When a treatment is given to cure inflammatory disorders such as otitis media, rhinitis and sinusitis, and such a physical condition as cerumen impaction in a department of otorhinolaryngology, for example, it is necessary to suction and thereby remove otorrhea, rhinorrhea and cerumen. The suction and removal conventionally uses a flexible tube having a length of about 1.5 to 2 meters and a suction tube for nose or ear attached to a tip part of the tube via an adaptor which are connected to a suction device of an otorhinolaryngology unit. These suction tubes having very small outer and inner diameters owing to the anatomical basis that they are to be inserted into a very narrow passage, however, were often clogged when the tenacious otorrhea, rhinorrhea and cerumen were sucked. The suction tube thus obstructed during the suction resulted in an extra and time-consuming work, which was to interrupt the treatment to replace the suction tube or unclog the suction tube by sucking a fluid having a low viscosity (for example, water) thereinto before restarting the treatment.

Japanese Patent No. 2742765 discloses a device wherein a suction tube cavity and a side tube cavity divided from each other by a mid partition wall are provided in a suction tube as a suction catheter for sucking and thereby removing a tenacious matter or fluid such as phlegm in bronchia, and at least a notch is formed in the mid partition wall to constitute a shunt path between the tube cavities. The suction catheter is adapted to apply a negative pressure to the suction tube cavity while supplying air and fluid such as a physiological salt solution from the side tube cavity. Thus constituted, a tip part of the catheter can be prevented from getting stuck in a bronchial lumen, and the tenacious matter such as phlegm is wetted to be easily sucked, as described in paragraph [0009] of Japanese Patent No. 2742765.

However, the comparative experiments carried out by the present inventors, which will be described later, revealed that the suction catheter recited in Japanese Patent No. 2742765 demands an extensive duration of time that may impose an excessive strain on a patient before the suction is completed in the case where, for example, a fluid having a high viscosity, for example, 500 cps is to be sucked.

SUMMARY OF THE INVENTION

An object of the present invention is to provide a suction device, a suction system, and a suction method capable of sucking and thereby removing a matter or fluid having a viscosity (hereinafter, simply referred to as a "viscous matter") without clogging a tube cavity in such an efficient manner that can dispense with any extra and time-consuming work.

To achieve the above object, a suction device of the present invention includes:

an outer tube connected to a fluid supply unit on a base-end side thereof and including an opening edge section; and a suction tube provided in the outer tube and connected to a negative pressure generating unit on a base-end side thereof, the suction tube including an opening edge section, wherein an annular fluid supply passage is formed between an inner peripheral surface of the outer tube and an outer peripheral surface of the suction tube, and the opening edge section of the suction tube placed inside the opening edge section of the outer tube toward a base-end side thereof.

A suction device of the present invention includes: a suction passage connected to a negative pressure generating unit on a base-end side thereof; and a fluid supply passage formed in an annular shape in an outer periphery of the suction passage and connected to a fluid supply unit on a base-end side thereof, wherein the suction device is adapted to suction a fluid supplied from the fluid supply passage when an object to be sucked is sucked into the suction passage in the form of a thin film so as to cover an entire inner peripheral surface of the suction passage.

A suction system of the present invention includes:

an outer tube including an opening edge section;

a suction tube including an opening edge section placed inside the opening edge section of the outer tube toward a base-end side thereof, the suction tube being provided in the outer tube so that an annular fluid supply passage is formed between an outer peripheral surface thereof and an inner peripheral surface of the outer tube; and a fluid supply unit connected to a base-end side of the outer tube; and a negative pressure generating unit connected to the base-end side of the suction tube.

A suction method comprising sucking an object to be sucked along with a fluid formed in the form of a thin film so as to cover an entire inner peripheral surface of a suction passage when the object to be sucked is sucked into the suction passage by an action exerted by a negative pressure.

In the suction device, suction system and suction method according to the present invention, the fluid may be water.

In the suction device and the suction system according to the present invention, the negative pressure generating unit may be a suction device for medical use, more particularly a suction device to be used in a department of otorhinolaryngology.

According to the suction device, suction system and suction method provided by the present invention, an entire inner peripheral surface of a suction tube is covered with a fluid in the form of a thin layer when a viscous matter to be sucked is sucked into the suction tube by an action exerted by a negative pressure, and a contact resistance of the viscous matter relative to the inner peripheral surface of the suction tube is significantly lessened on a principle similar to that of the hydroplaning phenomenon ("phenomenon in which a thin aqueous film formed between tires and a road surface when an automobile is running at a certain speed or higher makes it difficult for the tires to grip the road surface, thereby causing the automobile to be more likely to skid", the same also applies hereinafter in the description). As a result, the viscous matter can be sucked and thereby removed by the same suction force as that of any conventional device without clogging the suction tube in such an efficient manner that can dispense with any extra and time-consuming work.

BRIEF DESCRIPTION OF THE DRAWINGS

The present invention will become readily understood from the following description of preferred embodiments thereof made with reference to the accompanying drawings, in which like parts are designated by like reference numeral and in which:

FIGS. 5A to 5D are views illustrating changing processes of surface state of an aqueous solution having a high viscosity transferred downward when a conical tube is placed in an upright position.

DETAILED DESCRIPTION OF THE PREFERRED EMBODIMENTS

Hereinafter, an embodiment of the present invention is described with reference to the drawings.

Figure 1:
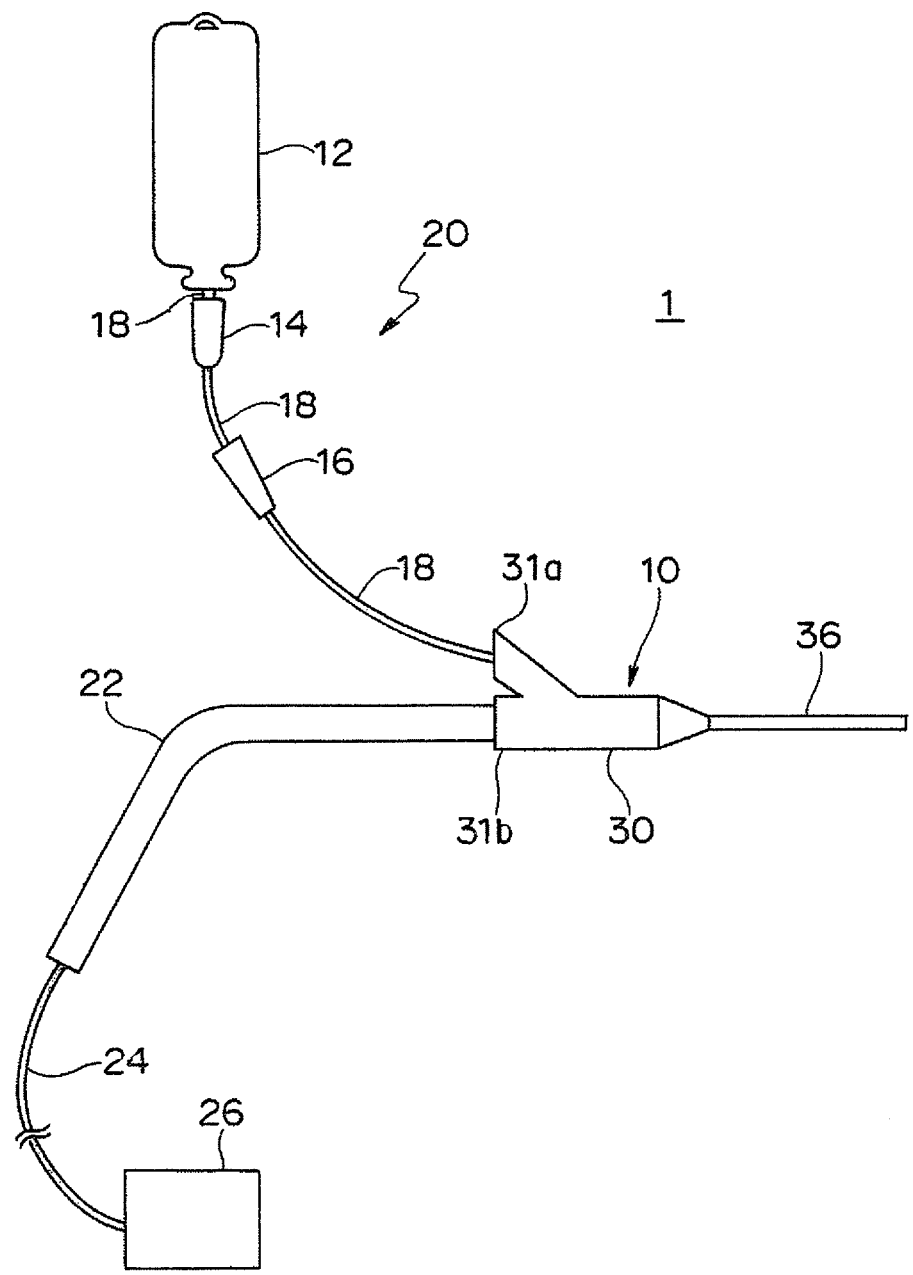
FIG. 1 is an overall view of a schematic structure of a suction system.

FIG. 1 is an overall view of a schematic structure of a suction system 1 for otorhinolaryngology according to one embodiment of the present invention.

The suction system 1 includes a suction device 10. A base end side of the suction device 10 is bifurcated into two end sections, and a fluid supply unit 20 is connected to a bifurcated end section 31a, while an end section of a handle unit 22 having such a pipe shape that bents in substantially an L shape is connected to another bifurcated end section 31b. The handle unit 22 is held by, for example, a doctor with his/her hand during suction. The shape of the handle unit 22 may be suitably altered into any other shape convenient for a user.

A drip infusion set conventionally used, including an infusion bag 12 containing a fluid having a low viscosity, an infusion cylinder 14, a roller flow rate adjustable valve 16, and a flexible tube 18 made of resin, can be used as the fluid supply unit 20. The fluid is preferably water which is inexpensively accessible and environment-friendly. However, the fluid is not necessarily limited to water (including an aqueous solution), and any fluid other than water may be used as far as it can exert the expected action and function of the present invention. In the suction device 1 according to the present embodiment, the drip infusion set is used as the fluid supply unit. However, the drip infusion set is not the only option, and anything available can be used as far as it can successively supply the fluid to the suction device 10.

Another end section of the handle unit 22 is connected to a negative pressure generating unit 26 by way of a flexible tube 24 made of PVC and having a length of, for example, 1.5 to 2 meters. The negative pressure generating unit 26 is conventionally provided with a negative pressure generating source such as a compressor, and a sucked matter reservoir such as a container. An example of the negative pressure generating unit 26 is a suction device of an otorhinolaryngology unit. When the negative pressure generating unit 26 thus constituted is operated, the viscous matter can be sucked from the edge section of the suction device 10 as described later.

Figure 2:
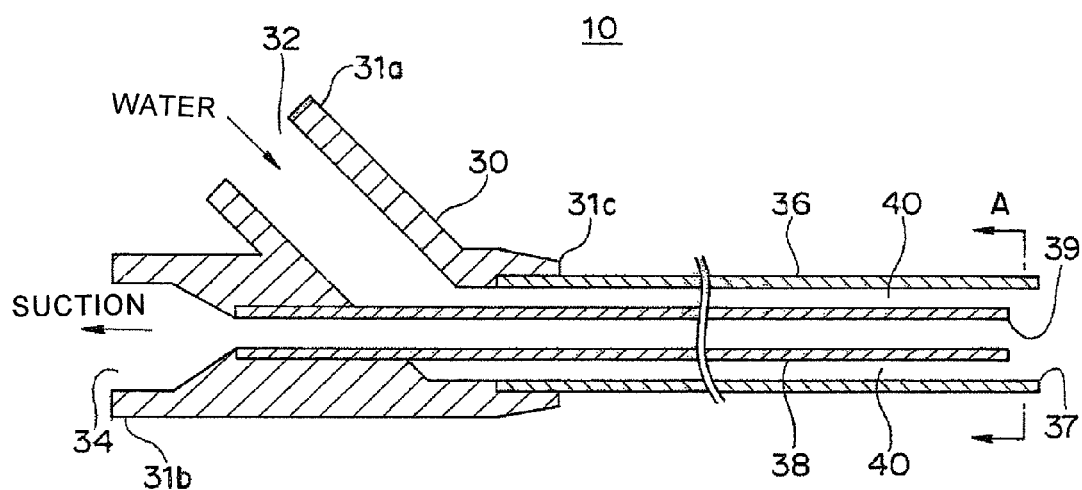
FIG. 2 is a longitudinal sectional view of a suction device.

FIG. 2 illustrates a sectional surface of the suction device 10. The suction device 10 includes an adapter unit 30 having the base end section bifurcated as described earlier, and an outer tube 36 and a suction tube 38 whose base end sections are secured to the adaptor unit 30. The adaptor unit 30 can be integrally provided and may be made of a material such as resin or rubber.

The adapter unit 30 includes a fluid supply port 32 at one of the bifurcated end sections, 31a, to be connected to the fluid supply unit 20, and a suction port 34 at the other bifurcated end section 31b to be connected to the negative pressure generating unit 26. A base end section of the outer tube 36 including an opening edge section 37 is securely connected to an edge section 31c of the adaptor unit 30. As the outer tube 36 can be used, for example, an outer sheath of 14G Surflow (registered trademark) needle (inner diameter of 1.73 mm, manufactured by Terumo Corporation).

Figure 3:
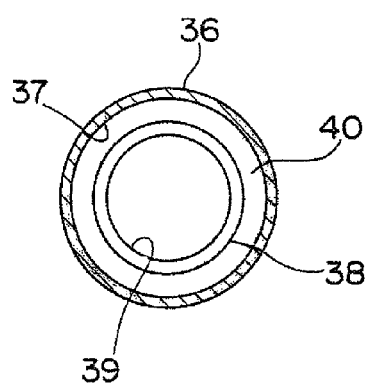
FIG. 3 is a sectional view taken along line A-A of FIG. 2.

The suction tube 38 whose inner cavity serves as a suction passage is provided in an inner cavity of the outer tube 36 to be concentric (or substantially concentric) thereto, and the suction tube 38 and the outer tube 36 constitute a double tube structure. Accordingly, an annular fluid supply passage 40 is formed between an inner peripheral surface of the outer tube 36 and an outer peripheral surface of the suction tube 38 as illustrated in FIG. 3. The fluid supply passage 40 communicates with the fluid supply port 32 of the adapter unit 30. The suction tube 38 communicates with the suction port 34 of the adapter unit 30 at the base end section thereof, and a negative pressure generated by the negative pressure generating unit 26 thereby acts on an opening edge section 39 of the suction tube 38 through the tube 24 and the handle unit 22. As the suction tube 38 can be used, for example, an inner needle of 16G Surflow (registered trademark) needle (outer diameter of 1.20 mm, inner diameter of 0.83 mm, manufactured by Terumo Corporation) from which a sharp edge section thereof is removed. The outer tube 36 and the suction tube 38 are not necessarily made of metal, and other examples of the usable material are resin and rubber.

As illustrated in FIG. 2, the suction tube 38 is provided so that the opening edge section 39 of the suction tube 38 is slightly placed inside the opening edge section 37 of the outer tube 36 toward the base end side thereof (for example, the opening edge section 39 of the suction tube 38 is placed about 1 mm from the opening edge section 37 of the outer tube 36). The opening edge section 39 of the suction tube 38 is thus positioned slightly more inward than the opening edge section 37 of the outer tube 36, so that, even if the opening edge section 37 of the outer tube 36 having contacted the viscous matter to be sucked is clogged, the viscous matter is guided from the fluid supply passage 40 over and around the opening edge section 39 of the suction tube 38, and then finally sucked into the suction tube 38.

A grinding member for finely grinding the matter to be sucked immediately before it is sucked (for example, rotating member having the shape of a propeller) may be provided in vicinity of the opening edge section 39 of the suction tube 38.

Figure 4A:
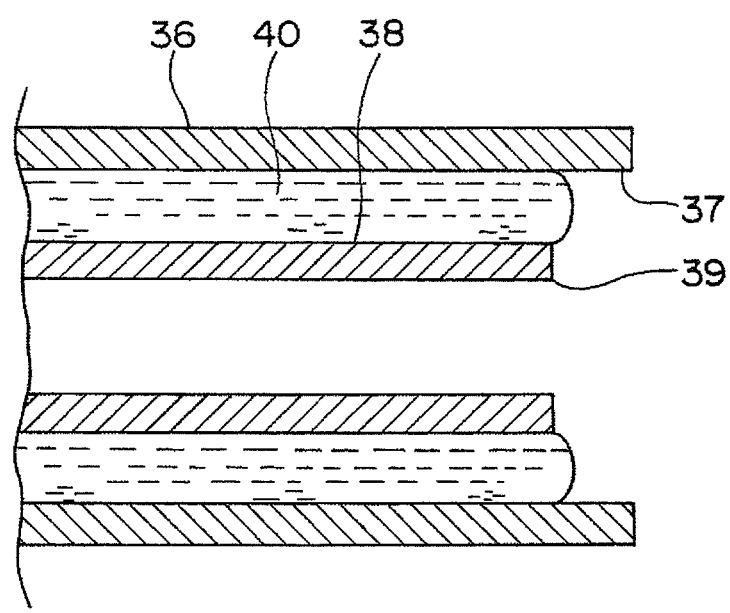
FIG. 4A is a view illustrating a state of water in a fluid supply passage when an opening edge section of an outer tube is open.

A suction operation by the suction system 1 thus constituted is described below. When a fluid having a low viscosity, such as water, is supplied from the fluid supply unit 20 to the fluid supply port 32 of the suction device 10, the supplied water is transferred to a distal end of the fluid supply passage 40 by the capillary as illustrated in FIG. 4A. The fluid (water) having transferred to the distal end of the fluid supply passage 40 may retain a state illustrated in FIG. 4A, or a very small amount of the fluid may be leaking from the fluid supply passage 40 when the negative pressure is not applied. In the case where, in the state described so far, the opening edge section 37 of the outer tube 36 stays open (in other words, the section not yet to contact or penetrate into the viscous matter to be sucked) even after the negative pressure generating unit 26 is activated, only air is sucked into the suction tube 38 with no predetermined negative pressure being applied to the vicinity of the opening edge section 39 of the suction tube 38. Therefore, the water currently staying in the fluid supply passage 40 is hardly sucked into the suction tube 39, which prevents the waste of water.

The earlier description mentioned water as an example of the fluid having a low viscosity. The water to be used is limited to neither ultrapure water nor pure water (distilled water, ion-exchanged water), and a physiological salt solution or an aqueous solution such as a lactated Ringer's solution can be used. The fluid having a low viscosity is not necessarily limited to water, and other fluids having a low viscosity, such as an organic solvent, can be used.

Figure 4B:
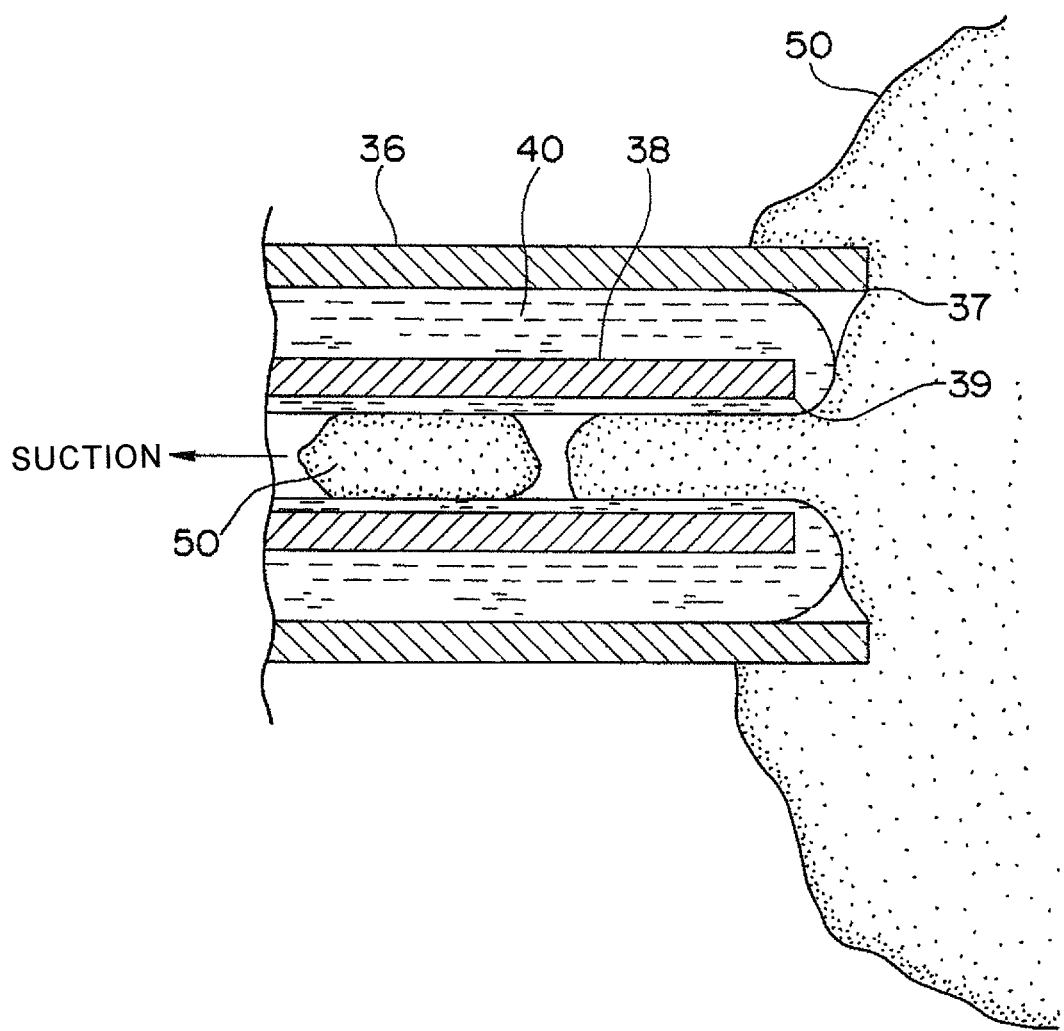
FIG. 4B is a view illustrating a state where the opening edge section of the outer tube contacts or penetrates into an object to be sucked and suction the object to be sucked.

When the opening edge section 37 of the outer tube 36 penetrates into a viscous matter 50 and is clogged therewith as illustrated in FIG. 4B, the predetermined negative pressure thereby acts on the vicinity of the opening edge section 39 of the suction tube 38. The viscous matter 50 is then sucked into the inner cavity of the suction tube 38. Further, the water in the fluid supply passage 40 is also sucked, along with the viscous matter 50, in such a state that covers the entire inner peripheral surface of the suction tube 38 in the shape of a thin film under the action of the negative pressure. Accordingly, a contact resistance of the viscous matter 50 relative to the inner peripheral surface of the suction tube 38 is significantly lessened on a principle similar to that of the hydroplaning phenomenon as compared with a case where the viscous matter is directly connected to the inner peripheral surface of the suction tube 38. As a result, the viscous matter 50 can be sucked and thereby removed by the suction force of the negative pressure generating unit 26 equal to that of any conventional device without clogging the suction tube 38 in such an efficient manner that can dispense with any extra and time-consuming work.

The suction system 1 according to the present embodiment can reduce the suction force required for the suction (that is negative pressure) as compared with the background art, for which an output of the compressor used in the negative pressure generating unit 26 can be accordingly reduced. These reductions allow the negative pressure generating unit 26 and therefore the suction system 1 to be more inexpensively obtained, and further lead to less power consumption.

As described earlier, the Surflow needles, which are commercially available and widely used, can be used in the production of the suction device 10. Therefore, production costs can be curtailed, or the suction device 10 can be more inexpensively obtained. As a result, the suction device 10 can be disposed after use.

As is clear from the following experiments, an amount of water, which is the fluid to be used when the viscous matter 50 is sucked, is distinctly reduced as compared with an amount of water to be used in water suction operation for unclogging the suction tube as mentioned in the description of the background art, and an amount of water to be used for washing the suction tube after sucking. Therefore, the device provided by the present invention is economically accessible and environment-friendly.

Experiments I, II and III

An experiment I was carried out to verify the effect of the suction system 1 according to the present embodiment. In a suction device used in the experiment I, the outer sheath of 14G Surflow needle was used as the outer tube, the inner needle of 16G Surflow needle, whose edge had been cut off, was used as the suction tube, and a joint member made of rubber which couples a base end section of the Surflow needle and a drip tube with each other in a drip infusion set was used as the adapter unit. A drip infusion set for pediatric use was used as the fluid supply unit, and water was used as the fluid to be supplied. Further, a diaphragm dry vacuum pump DAP-30 manufactured by ULVAC KIKO, Inc. was used as the negative pressure generating source, an Erlenmeyer flask was used as the sucked matter reservoir.

As the viscous matter to be sucked was used three different sodium alginate aqueous solutions respectively having different percentages by weight, 2% by weight, 3% by weight, and 4% by weight. Hereinafter, the aqueous solutions are respectively referred to as 2% aqueous solution, 3% aqueous solution and 4% aqueous solution. The sodium alginate powder used in the experiment was a product code: 31131-85 manufactured by Nacalai Tesque, The water in which the sodium alginate is to be dissolved was Milli-Q water (ultrapure water).

The 2%, 3% and 4% aqueous solutions were prepared as described below and used. The sodium alginate powders respectively having the weights of 0.4 g, 0.6 g and 0.8 g were weighted, put in three conical tubes (capacity: 50 cc) each containing 20 ml of water, and then adequately stirred therein. The conical tubes were thereafter left in a dark and cool place for 24 hours. After it was visually confirmed that the respective powders were completely dissolved, they were further stirred long enough to eliminate any irregularity in their concentrations. Then, the obtained solutions were sterilized by ultraviolet ray for about 20 to 30 minutes, and then left in a dark and cool place for six days before they were used in the experiment.

The manufacturer' data (Nacalai Tesque, Inc.) says that the viscosity of the 1% sodium alginate aqueous solution used in the experiment is about 500 cps, however, they fail to provide any data relating to the viscosities of the 2%, 3% and 4% aqueous solutions. Moreover, the viscosities of the respective aqueous solutions could not be measured by a viscosity indicator, resulting in the failure to quantify the viscosities using specific numeral values. One thing for certain is that, however, the viscosity of the 2% aqueous solution is higher than that of the 1% aqueous solution. Moreover, the visual confirmation indicated that the viscosity of the 3% aqueous solution was higher than that of the 2% aqueous solution, and the viscosity of the 4% aqueous solution was higher than that of the 3% aqueous solution.

At normal temperature, conical tubes 52 respectively containing the prepared aqueous solutions in a state illustrated in FIG. 5A were placed in an upright position as illustrated in FIG. 5B, and the followings were measured, respectively: a first time required for the transition of an aqueous solution surface W to a state illustrated in FIG. 5C (center of the surface is flat); and a second time required for the transition of the surface W to a state illustrated in FIG. 5D (entire surface is flat), right after the conical tubes 52 took the upright position. The result thereby obtained showed that the first time was about 30 seconds and the second time was about two minutes for the 2% aqueous solution, the first time was about 60 seconds and the second time was about three minutes for the 3% aqueous solution, and the first time was about 120 seconds and the second time was about six minutes for the 4% aqueous solution. This information is importantly useful for estimating the viscosities of the respective aqueous solutions.

As comparative experiments were also carried out: an experiment II which performed the suction using the same suction device as that of the experiment I with no water supply; and an experiment III which performed the suction using only an aluminum pipe having the inner diameter of 2 mm and the length equal to that of the suction tube of the suction device used in the experiment I (88 mm), which was directly attached to the handle unit as the suction tube.

In the experiments I, II and III, amounts of time respectively necessary for completing the suction of 20 ml of the 2% and 3% and 4% sodium alginate aqueous solution were measured. The following Table 1 shows the measured necessary amounts of time.

TABLE 1

| Experiment | 2% aqueous solution | 3% aqueous solution | 4% aqueous solution |
|---|---|---|---|
| I | 38 seconds | 50 seconds (first time), 52 seconds (second time) | 98 seconds (first time), 90 seconds (second time) |
| II | 404 seconds | — (Suction not performed due to anticipated difficulty) | — (Suction not performed due to anticipated difficulty) |
| III | 83 seconds | 699 seconds | 3832 seconds (calculated from 958 seconds for 5 ml) |

The result shown in Table 1 evidently confirmed that the suction system 1 according to the present embodiment is distinctly advantageous in its performance of sucking and thereby removing the highly viscous matter to be sucked in a short period of time. As compared with the experiment II, in particular, it was verified that the contact resistance of the matter to be sucked relative to the inner peripheral surface of the suction tube is remarkably lessened by the water running in the suction tube so as to cover the inner peripheral surface thereof in the form of a thin film.

The amounts of water used in the experiment I were less than 1 ml for the 2% aqueous solution, 3 ml for the 3% aqueous solution, and about 6 to 8 ml for the 4% aqueous solution. Thus, it was confirmed such a small amount of water was used in any of these aqueous solutions.

Experiment IV

To verify the distinctly different effect of the suction system 1 according to the present embodiment, a suction device having a structure substantially identical to that of the suction catheter recited in Japanese Patent No. 2742765 was manufactured, so that an experiment IV for the suction of the 2% sodium alginate aqueous solution was carried out in a manner similar to the experiment I.

The suction device used in the experiment IV was manufactured as follows. First, a 3Fr polyethylene tube (outer diameter of about 1 mm, inner diameter of about 0.5 mm) as the side tube was securely bonded to the outer sheath of 16G Surflow needle as the suction tube in parallel therewith, and an edge section thereof was cut off so that positions of the opening edge sections of the two tubes were aligned. Then, a notch was formed with a sharp cutting tool in walls of the two tubes at a section where these tube walls contact each other so as to form a shunt path for communicating inner cavities of the two tubes with each other.

The suction device thus manufactured was coupled with the handle unit to carry out the experiment to suction the 2% aqueous solution (20 ml) in a manner similar to the experiment I. In an initial stage of the experiment, the aqueous solution was sucked with air being supplied to the side tube, however, the experiment was discontinued since it took 637 seconds to suction only about 5 ml. A simple calculation based on the fact indicates that it takes 2,548 seconds, which is four times longer, to suction 20 ml of the 2% aqueous solution.

Next, a similar suction experiment was carried out with water being supplied to the side tube, wherein it took 321 seconds to complete the suction, and an amount of water used then was 7 ml. In contrast, the amount of water used in the suction device according to the present embodiment was less than 1 ml with the required time of 38 seconds as shown in Table 1. These data proved that the suction device according to the present embodiment is highly capable by comparison in its performance of sucking the highly viscous matter, and consumed only the very small amount of water.

The experiment IV passed the suction of the 3% and 4% aqueous solutions because it was easily anticipated that these aqueous solutions would be difficult to suction.

The suction catheter recited in Patent Document 1 did solve the problem that the tip part of the catheter possibly gets stuck in a bronchial lumen, however, it appears that the suction force to be thereby exerted is relatively weakened by its given structure where the fluid flows into the suction tube from the side tube through the shunt path. The suction catheter thus constituted can no way suction the fluid drawn into the suction tube through one (or a plurality of) shunt path and running therein so as to cover the entire inner peripheral surface of the suction tube in the form of a thin film. Therefore, it is concluded that the suction catheter is totally different to the suction device according to the present invention.

Experiments V, VI and VII

In an suction experiment V for verifying the effect of the suction system 1 according to the present embodiment, a suction device 10 having a double tube structure, in which a suction tube (outer diameter of 1.20 mm, inner diameter of 0.83 mm) 38 was provided in the inner cavity of the outer tube (inner diameter of 1.73 mm) 36 to be concentric (or substantially concentric) to the outer tube 36, was used in a manner similar to the experiment 1. As the viscous matter to be sucked were used three different sodium alginate aqueous solutions respectively having different percentages by weight, 2% by weight, 3% by weight and 4% by weight. In the experiment, water was supplied from the fluid supply unit 20 to between the outer tube 36 and the suction tube 38 through the fluid supply port 32 and the fluid supply passage 40 during the suction in a manner similar to the experiment 1.

As comparative experiments were also carried out: "same length with larger diameter (experiment VI)" wherein only an aluminum pipe having the inner diameter of 2 mm and the length equal to that of the suction tube of the suction device used in the experiment V (88 mm) was directly attached to the handle unit 22 as the suction tube and used for the suction, and "no water supply (experiment VII)" wherein the same suction device as that of the experiment V was used for the suction with no water supply. In the case of the "same length/larger diameter (experiment VI)" wherein the outer tube was not provided, there was no water supply because the suction tube alone was used for the suction.

In the "experiment V", "same length with larger diameter (experiment VI)" and "no water supply (experiment VII)", amounts of time required for completing the suction of 20 ml of the 2%, 3% and 4% sodium alginate aqueous solutions were measured. The measured required amounts of time are shown in the following Table 2. The experiments V, VI and VII could not arrange the same experimental conditions as those of the experiments I, II and III, such as temperature, humidity and suction device to be used. Therefore, it is inappropriate to equally evaluate results obtained from these experiments and the results of the experiments I, II and III. The group of experiments (I, II and III) and the group of experiments (V, VI and VII) should be carried out under exactly the same conditions so that they can be properly compared to each other.

TABLE 2

| | Experiment V | | Same length with larger diameter (experiment VI) | No water supply (experiment VII) |
|---|---|---|---|---|
| Concentration | Suction time | Amount of water used for suction | | |
| 2% | 49 seconds | 1 ml | 84 seconds | 435 seconds |
| 2% | 59 seconds | 1 ml | 82 seconds | 371 seconds |
| 2% | 69 seconds | 1 ml | 94 seconds | 359 seconds |
| 2% | 48 seconds | 1 ml | 98 seconds | 300 seconds |
| 3% | 104 seconds | 2 ml | 414 seconds | 1577 seconds |
| 3% | 110 seconds | 3 ml | 482 seconds | 2191 seconds |
| 3% | 102 seconds | 2 ml | 393 seconds | 2158 seconds |
| 3% | 48 seconds | 1 ml | 369 seconds | 2150 seconds |
| 4% | 203 seconds | 3 ml | 1383 seconds | No experiment carried out |
| 4% | 184 seconds | 5-7 ml | 1108 seconds | No experiment carried out |
| 4% | 178 seconds | 5 ml | 1065 seconds | No experiment carried out |

Table 3 shows averages and standard deviations of the required times for the respective concentrations in the experiments V, VI and VII.

TABLE 3

| Concentration | Experiment V | Same length with larger diameter (experiment VI) | No water supply (experiment VII) |
|---|---|---|---|
| | Average value | | |
| 2% | 56.3 seconds | 89.5 seconds | 366.3 seconds |
| 3% | 91.0 seconds | 414.5 seconds | 2019.0 seconds |
| 4% | 188.3 seconds | 1185.3 seconds | — |
| | Standard deviation | | |
| 2% | 9.8 seconds | 7.7 seconds | 553 seconds |
| 3% | 28.9 seconds | 48.6 seconds | 295.2 seconds |
| 4% | 13.1 seconds | 172.5 seconds | — |

The results obtained from the experiments V, VI and VII, confirmed that the suction system according to the present embodiment is distinctly advantageous in its performance of sucking and thereby removing the highly viscous matter to be sucked in a short period of time. As compared with the "no water supply (experiment VII), in particular, it was verified that the contact resistance of the matter to be sucked relative to the inner peripheral surface of the suction tube is significantly lessened by the water running in the suction tube so as to cover the inner peripheral surface thereof in the form of a thin film. Further, as compared with the "same length with larger diameter (experiment VI)" wherein it appears that the sucking can be facilitated by the larger diameter", the suction system used in the experiment V clearly demonstrates its higher efficiency in sucking the highly viscous matter to be sucked with the water running on the inner peripheral surface of the suction tube in the form of a thin film.

The amounts of water used in the experiment V were about 1 ml for the 2% aqueous solution, 1 to 3 ml for the 3% aqueous solution, and about 3 to 5 ml for the 4% aqueous solution. Thus, it was confirmed such a small amount of water was used in any of these aqueous solutions.

The present invention was described referring to the suction device, suction system and suction method for otorhinolaryngology, which represented an embodiment thereof. However, the present invention is not necessarily limited to the treatment to be provided in otorhinolaryngology, and can be applied to a suction device used in clinical practice of a different medical field (for example, surgery).

Moreover, the suction device and the like according to the present invention are not necessarily limited to medical use, and can be suitably used in, for example, a work site where it is necessary to suction viscous matters such as sludge and oil. Thus, the present invention has a broad range of application.

The invention claimed is:

1. A suction device, comprising:
an outer tube including a base-end side and an opening edge section, the outer tube being connected to a fluid supply unit on the base-end side of the outer tube;
a suction tube provided in the outer tube and including a base-end side and an opening edge section, the suction tube being connected to a negative pressure generating unit on the base-end side of the suction tube,
wherein an annular fluid supply passage, configured to supply fluid from a distal end thereof, is formed between an inner peripheral surface of the outer tube and an outer peripheral surface of the suction tube, and
the opening edge section of the suction tube is placed inside the opening edge section of the outer tube toward the base-end side thereof; and
an adapter connected to the base-end side of the outer tube and the base-end side of the suction tube, the adapter having a fluid supply port that connects the outer tube to the fluid supply unit and a suction port that connects the suction tube to the negative pressure generating unit,
wherein the annular fluid supply passage is configured to allow the fluid to exit the distal end thereof in a direction along a longitudinal axis of the outer tube, and
the opening edge section of the suction tube is spaced from the opening edge section of the outer tube to define an annular fluid exit at the distal end of the annular fluid supply passage.

2. The suction device according to claim 1, wherein the fluid is water.

3. The suction device according to claim 1, wherein the negative pressure generating unit is a suction device for medical use.

4. The suction device according to claim 3, wherein the suction device for medical use is a suction device for otorhinolaryngology.

5. A suction device, comprising:
a suction tube having a suction passage connected to a negative pressure generating unit on a base-end side thereof;
an outer tube having a fluid supply passage, configured to supply fluid from a distal end thereof, formed in an annular shape at an outer periphery of the suction passage and connected to a fluid supply unit on a base-end side thereof, an opening edge section of the suction tube being spaced from an opening edge section of the outer tube, to define an annular fluid exit at the distal end of the annular fluid supply passage,
wherein the suction device is adapted to suck a fluid supplied from the fluid supply passage into the suction passage, such that the fluid is sucked in the form of thin layer over the entire inner peripheral surface of the suction passage, when an object to be sucked; and
an adapter connected to the fluid supply passage and the suction passage, the adapter having a fluid supply port that connects the fluid supply passage to the fluid supply unit and a suction port that connects the suction passage to the negative pressure generating unit.

6. The suction device according to claim 5, wherein the fluid is water.

7. The suction device according to claim 5, wherein the negative pressure generating unit is a suction device for medical use.

8. The suction device according to claim 7, wherein the suction device for medical use is a suction device for otorhinolaryngology.

9. The suction device according to claim 5, wherein the annular fluid supply passage is configured to allow the fluid to exit the distal end thereof in a direction along a longitudinal axis of the outer tube.

* * * * *